US00PP24832P2

(12) United States Plant Patent
Ehlenfeldt

(10) Patent No.: US PP24,832 P2
(45) Date of Patent: Sep. 2, 2014

(54) BLUEBERRY PLANT NAMED 'NOCTURNE'

(50) Latin Name: ***Vaccinium*×hybrid**
Varietal Denomination: Nocturne

(71) Applicant: The United States of America, as represented by the Secretary of Agriculture, Washington, DC (US)

(72) Inventor: Mark K Ehlenfeldt, Tabernacle, NJ (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 123 days.

(21) Appl. No.: 13/573,631

(22) Filed: Sep. 28, 2012

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

2008/0209600 P1 8/2008 Patel

*Primary Examiner* — Annette Para
(74) *Attorney, Agent, or Firm* — Gail E. Poulos; John D. fado; Lesley M. Shaw

(57) ABSTRACT

A new and distinct hexaploid hybrid blueberry (*Vaccinium*× hybrid) cultivar named Nocturne. Nocturne is a hybrid with complex hexaploid ancestry, derived from *V. ashei* Reade, *V. constablaei* Gray, *V. corymbosum* L., *V. darrowii* Camp, *V. angustifolium* Ait., and *V. tenellum* Ait.,. It is cold hardy, having an extended dormancy period, and a late flowering interval, is productive year-after-year, consistently producing 12-13 lbs. of fruit per plant, it has ripe fruit that is large, dark, and sweet that ripens in mid-July in New Jersey and the fruit are tinted vivid, red-orange when unripe, and ripen to black. Nocturne is a vigorous upright plant with glossy, medium-green foliage, and a somewhat sprawling habit.

7 Drawing Sheets

Latin name of the genus and species of the plant claimed: 'Nocturne' is a new blueberry plant that is a *Vaccinium*× hybrid.

Variety denomination: The new blueberry plant claimed is of the variety denominated 'Nocturne', *Vaccinium*×hybrid.

BACKGROUND OF THE INVENTION

The present invention relates to the discovery of a new and distinct variety of blueberry plant selected in 1999 at the Marucci Center for Blueberry & Cranberry Research and Extension, Chatsworth, N.J. Nocturne is a hybrid with complex hexaploid ancestry, derived from *V. ashei* Reade, *V. constablaei* Gray, *V. corymbosum* L., *V. darrowii* Camp, *V. angustifolium* Ait., and *V. tenellum* Ait., is cold hardy, having an extended dormancy period, and a late flowering interval; productive year-after-year, consistently producing 12-13 lbs. of fruit per plant; ripe fruit is large, dark, and sweet that ripens in mid-July in New Jersey; fruit are tinted vivid, red-orange when unripe, and ripen to black, and is a vigorous upright plant with glossy, medium-green foliage, and a somewhat sprawling habit.

The new and distinct variety of blueberry plant Nocturne was selected from a seedling population of the cross US 874×'Premier' in 1999 at the Marucci Center for Blueberry & Cranberry Research and Extension, Chatsworth, N.J. Asexual reproduction of the new cultivar Nocturne by vegetative cuttings was performed at Chatsworth, N.J. beginning in 2005.

The following traits for Nocturne are determined to be the basic characteristics of the new cultivar which distinguish this blueberry plant as a new and distinct when compared to other blueberry varieties, including it's parent 'Premier', and Nocturne's offspring T-885 ('SUMMER SUNSET'™), known to the breeder:

1) a hybrid with complex hexaploid ancestry, derived from *V. ashei* Reade, *V. constablaei* Gray, *V. corymbosum* L., *V. darrowii* Camp, *V. angustifolium* Ait., and *V. tenellum* Ait.,
2) cold hardy, having an extended dormancy period, and a late flowering interval
3) productive year-after-year, consistently producing 12-13 lbs. of fruit per plant,
4) ripe fruit that is large, dark, and sweet that ripens in mid-July in New Jersey,
5) fruit that are tinted vivid, red-orange when unripe, and which ripen to black, and
6) a vigorous upright plant with glossy, medium-green foliage, and a somewhat sprawling habit.

The new variety is designated Nocturne.

BRIEF DESCRIPTION OF THE PHOTOGRAPHS

DETAILED DESCRIPTION OF THE NEW CULTIVAR

Figure 1:
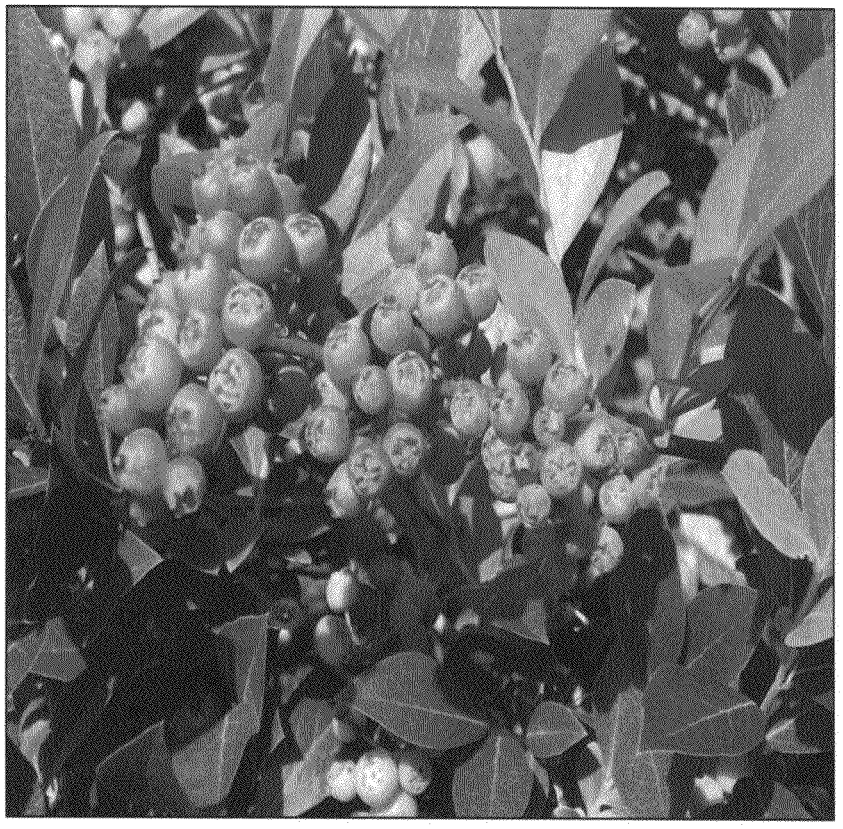
FIG. 1 is a color photograph which shows the red-orange of unripe fruit of Nocturne.
Figure 2:
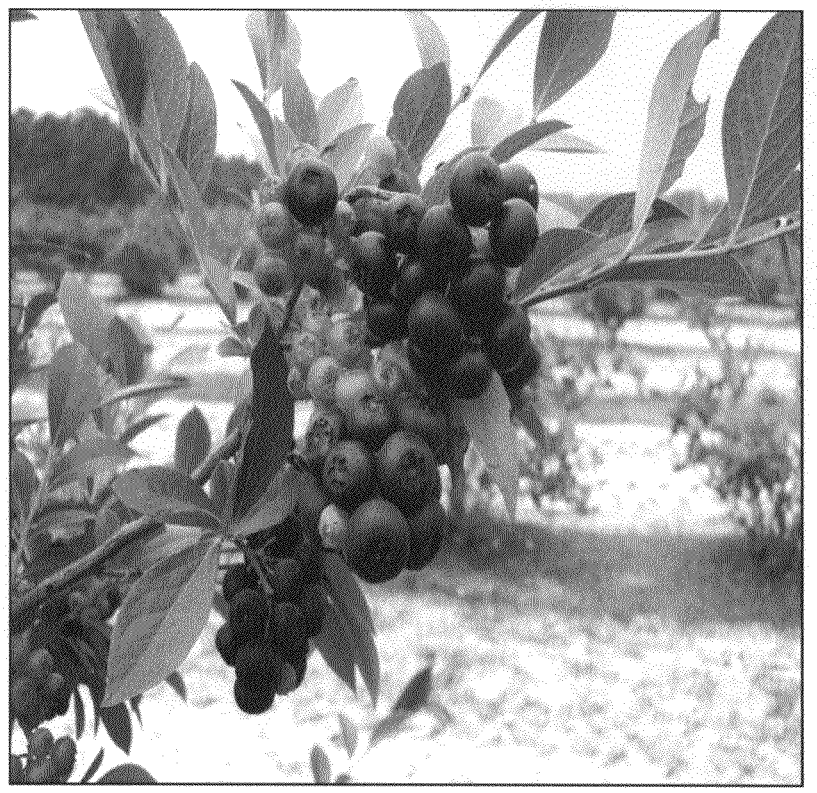
FIG. 2 is a color photograph which shows the large, dark ripe fruit and orange-red unripe fruit of Nocturne.
Figure 3:
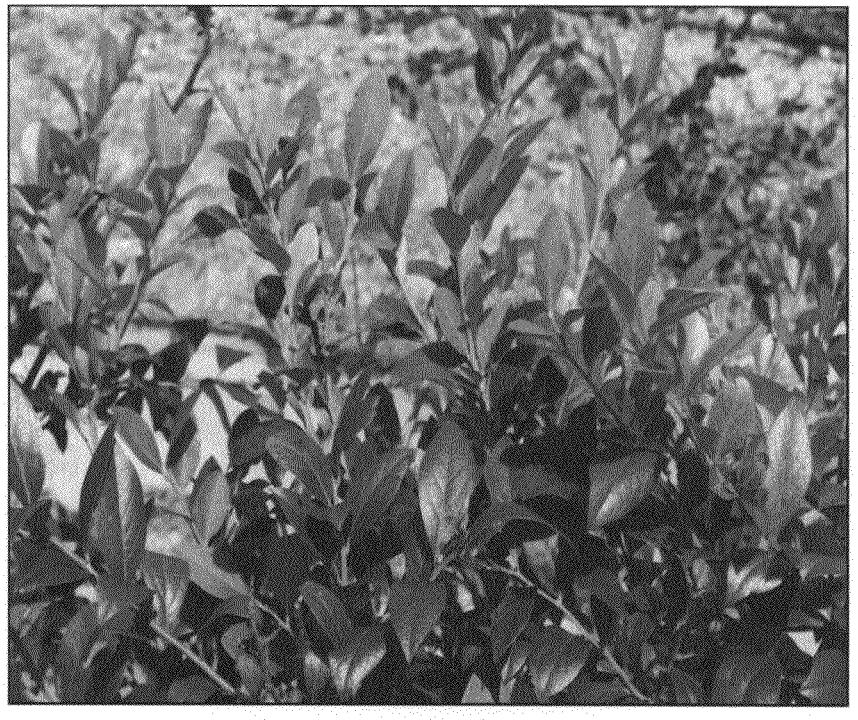
FIG. 3 is a color photograph which shows the upper surface of mature leaves of Nocturne.
Figure 4:
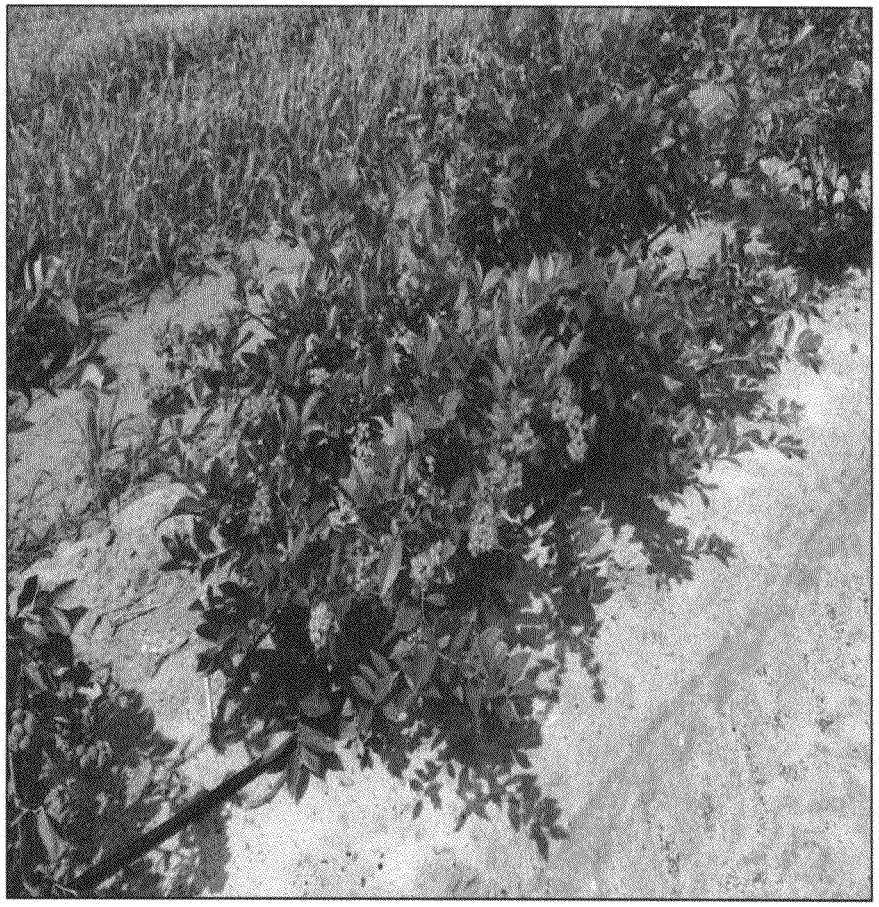
FIG. 4 is a color photograph which shows a 3-year old plant of Nocturne.
Figure 5:
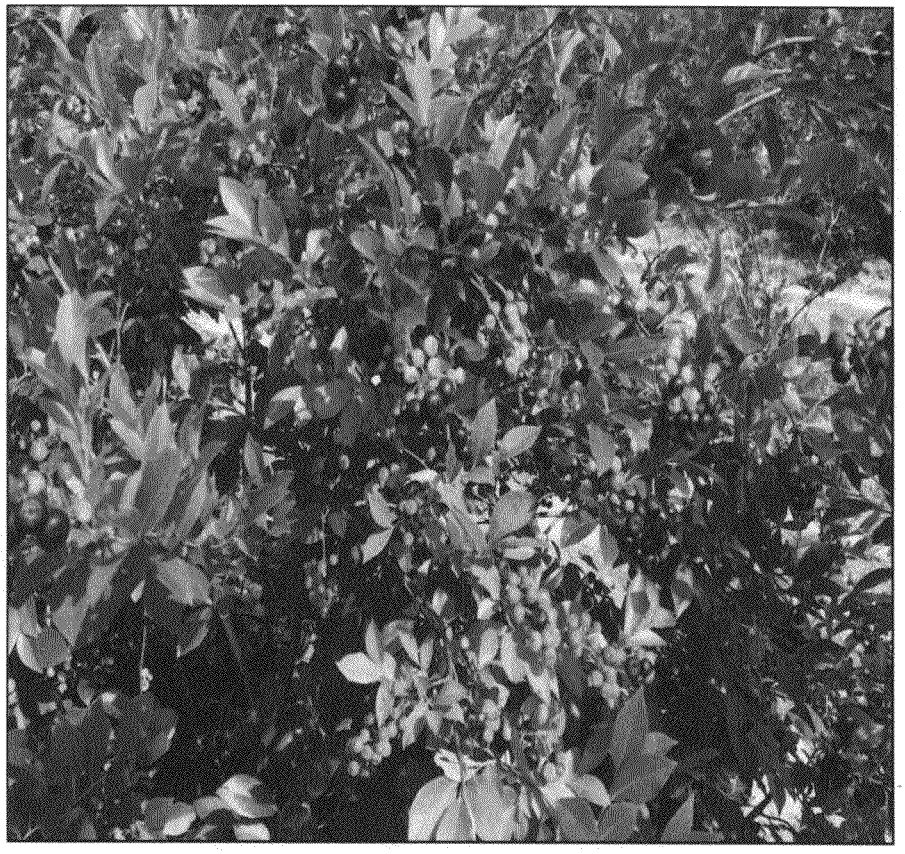
FIG. 5 is a color photograph which shows a section of a mature plant of Nocturne that is 7-years old.
Figure 6:
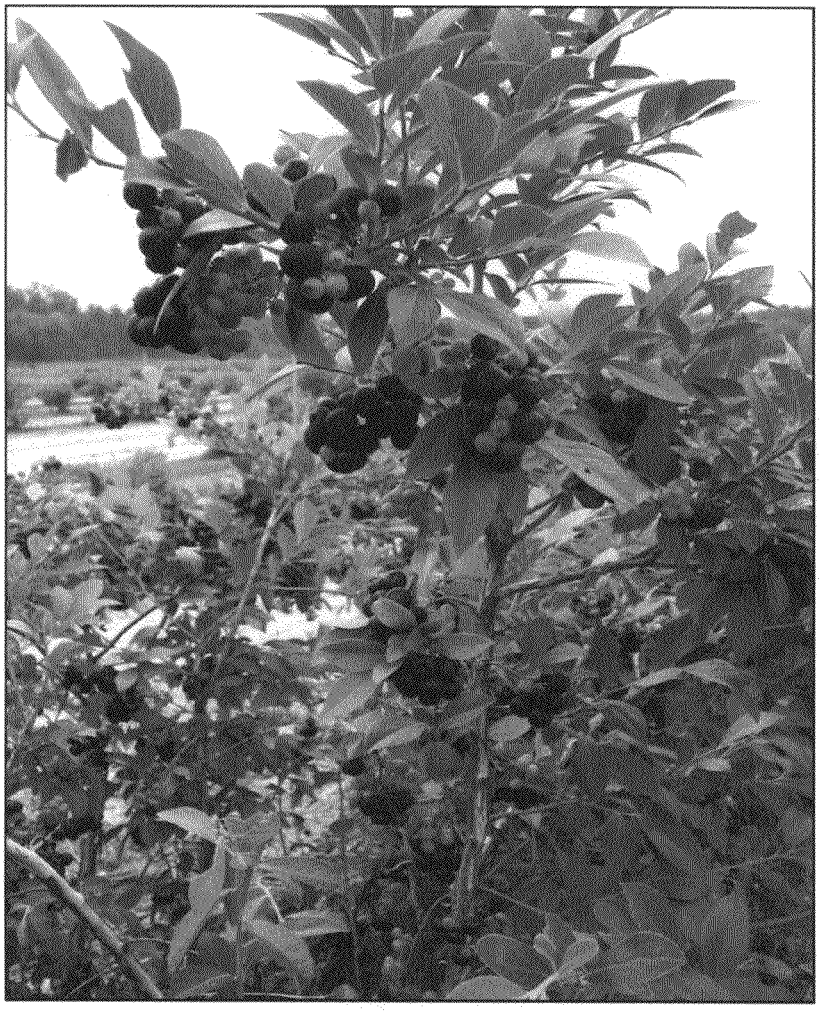
FIG. 6 is a color photograph which shows a mature plant of Nocturne with abundant ripe and unripe fruit.
Figure 7:
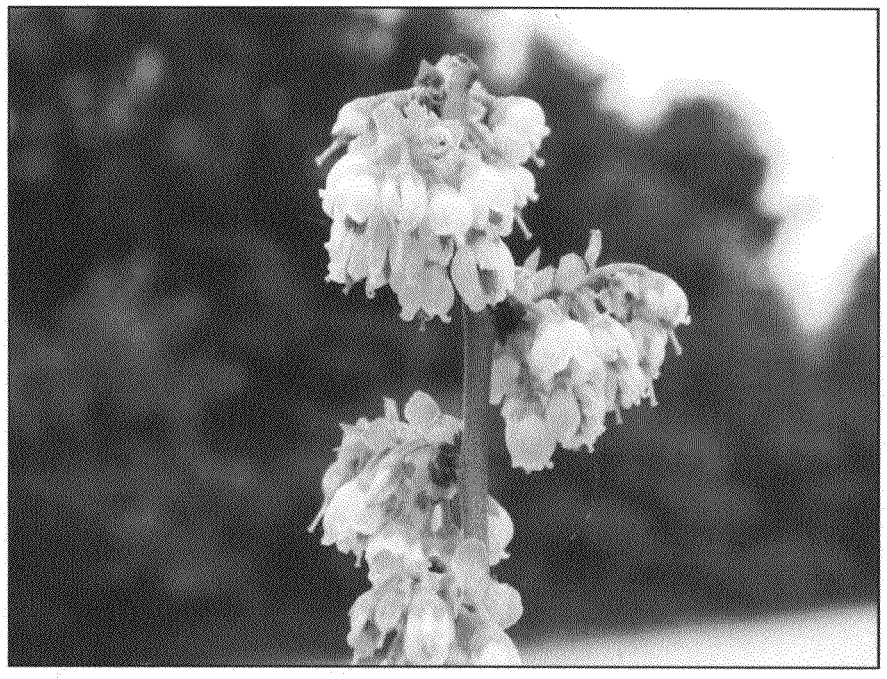
FIG. 7 is a color photograph which shows the flowers of Nocturne.

The following is a detailed description of the botanical and pomological characteristics of the subject blueberry plant. Color data (except those in common terms) are described from "The Pantone Book of Color", published by H. N. Abrams, Inc., N.Y. 2000

Where dimensions, sizes, colors and other characteristics are given, it is to be understood that such characteristics are approximations of averages set forth as accurately as practicable.

Nocturne can be compared to its rabbiteye parent, the cultivar 'Premier', and a recently patented cultivar T-885 ('Summer Sunset' ™) which is an offspring of Nocturne×'Climax'. Nocturne is a vigorous, upright plant with a moderate suckering tendency, and a somewhat sprawling habit. 'Premier' and T-885 both are generally upright with narrow bases with only minor suckering tendencies.

Plant characteristics were measured on 7-year old plants planted in unamended soil in a field in Chatsworth, N.J. The plants were provided with overhead irrigation and fertilized according to commercial practices.

Bush:

*Plant height*.—Approximately 1.5 m.

*Canopy*.—Approximately 1.7 m. Diameter was measured at the widest part of the bush.

*Plant vigor*.—High.

*Growth habit*.—Between spreading and upright.

*Flower bud density*.—(Number) along flowering twigs in January — High.

*Twigginess*.—Medium.

*Overall survival in field*.—High.

*Ease of propagation*.—Easy to propagate.

Trunk/canes:

*Suckering tendency*.—Medium.

*Surface texture of 6-month-old stems observed September 20*.—Smooth.

*Surface texture of strong, 1-year-old shoots observed in September*.—Changing from smooth to rough. Vertical cracks appear in the smooth stems. A rough corky growth fills these cracks. By the time the canes are 3 years old, the rough, corky material has exfoliated and the stems are again essentially smooth. This is a normal pattern of stem thickening in rabbiteye blueberry.

*Surface texture of 3-year-old canes*.—Relatively smooth, slightly exfoliating.

*Color of 6-month-old smooth stems spring (sunny side)*.—Pantone 119M (medium drab green).

*Color of 6-month old smooth stems spring (shady side)*.—Pantone 499M (maroon).

*Color of 2-year-old rough, corky canes*.—Pantone 730M (a shade of coppery brown).

*Color of 3-year-old smooth canes after exfoliation*.—Pantone 402M (medium grey).

Leaves:

*Leaf length for fully expanded leaves including petiole*.—Approximately 7-8 cm.

*Leaf width for fully expanded leaves*.—Approximately 3-3.5 cm, average 3.25 cm.

*Leaf shape*.—Obovate.

*Leaf margin*.—Very finely serrate.

*Color of upper surface of mature leaves*.—Pantone 380 M (bright green).

*Color of upper surface of young leaves*.—Pantone 579 M (pale green).

*Pubescence on upper surface of leaves*.—Non.

*Pubescence on lower surface of leaves*.—Short, fine pubescence on midrib and adjacent parts of veins; otherwise glabrous.

*Pubescence on leaf margins*.—None.

Flowers:

*Flower arrangement*.—Flowers arranged alternately along a short, leafless, deciduous branch.

*Flower cluster*.—Medium to open.

*Number of flowers per cluster*.—Approximately 8-14, mean 11.

*Fragrance*.—None.

*Flower type*.—Perfect, ovary inferior, petals fused into a corolla tube, the 10 stamens inserted at the base of the corolla tube.

*Petals*.—Fused into a corolla tube with 5 lobes.

*Flower shape*.—Spherical, balloon-like, but often partially distorted, split, and/or missing segments.

*Corolla surface texture*.—Smooth.

*Corolla color at anthesis*.—Pantone 1M (cool gray) tinged with Pantone 488 M (pale pink).

*Calyx color at anthesis*.—Pantone 365 M (light green) tinged with Pantone 7515 M (light pink).

*Pedicel length at time of anthesis*.—7-10 mm.

*Peduncle length at time of anthesis*.—11-20 mm.

*Flower length, pedicel attachment point to corolla tip*.—Average 9 mm.

*Style length, top of ovary to stigma tip*.—Average 12 mm.

*Calyx diameter at anthesis*.—4-5 mm.

*Diameter of corolla tube at widest point*.—Average 9 mm.

*Corolla aperture diameter*.—Average 5 mm.

*Location of tip of style relative to lip of corolla*.—Stigma tip extends 3 mm beyond corolla tube.

*Flowering period*.—Date of 50% open flower averages about May 15 in Chatsworth, N.J., which is 1-2 weeks later than typical highbush varieties. Comparisons to other rabbiteye cultivars are difficult since many are not cold hardy in N.J.

*Pollen staining*.—Greater than 90% of the grains stain with acetocarmine dye, indicating that a high percentage of the pollen grains are normal, plump, and potentially viable.

*Pollen abundance*.—Dried flowers shed pollen abundantly.

*Self-fruitfulness*.—Medium to high (70% fruit set in a greenhouse study); much higher than typical rabbiteye which has almost no self fertility.

Fruit: Nocturne has fruit that are tinted vivid, red-orange [Pantone 7416 M] when unripe, and which ripen to black [Pantone 431 M]. 'Premier' has a pinkish [Pantone 694 M] cast to unripe fruit and ripens to medium blue. T-885 (Summer Sunset™) is similar in most coloration aspects to Nocturne.

*Berry color (unripe)*.—Pantone 458 M (yellow-green).

*Berry color (intermediate)*.—Pantone 7416 M (typical, coral).

*Berry color (turning)*.—Pantone 703 M (reddish).

*Berry color* (*ripe*) *on plant*.—Pantone 431 M (typical, gunmetal) to Pantone 536 M (blue-black).

*Berry surface wax*.—Sparse to low in abundance.

*Mean berry width*.—13-16, mean 14.6 mm.

*Mean berry height*.—10-11, mean 10.3 mm.

*Mean berry weight on well-pruned plants*.—2.0 g.

*Diameter of calyx aperture on mature berry*.—4-5 mm.

*Calyx lobes on mature berry size and shape*.—Calyx lobes small, resulting in a calyx aperture that is nearly round. Calyx lobes appressed to the surface of the berry.

*Pedicel length on ripe berry*.—7-11 mm.

*Berry pedicel scar*.—Small and dry.

*Peduncle length at the time berries are ripe*.—11-20 mm.

*Berry cluster* (*tight, medium, or open*).—Medium.

*Berry firmness*.—Medium, similar to the highbush cultivar 'Bluecrop'.

*Berry flavor*.—Sweet with moderate acidity; flavor atypical for either highbush or rabbiteye.

*Berry texture*.—Smooth; seeds small and grit (stone cells) not noticeable.

*Mean date of* 50% *fruit ripe*.—July 11. This is earlier than virtually all other typical rabbiteye, and is mid-late season compared to highbush.

*Fruit storage capability*.—Moderate.

Disease resistance:

*Red ringspot virus*.—Resistant.

*Mummy berry blight*.—Moderately resistant.

*Mummy berry fruit infection*.—Resistant.

I claim:

1. A new and distinct rabbiteyed-derived, hexaploid blueberry plant as illustrated and described, characterized by being very cold hardy, having a long dormancy period, possessing a vigorous bush, colorful unripe fruit, and large, sweet, dusky black fruit when fully ripe.

* * * * *